United States Patent
Zhang

(10) Patent No.: US 7,217,824 B2
(45) Date of Patent: May 15, 2007

(54) PROCESS FOR PREPARING A 4,7-BIS(5-HALOTHIEN-2-YL)-2,1,3-BENZO-THIADIAZOLE AND A PRECURSOR THEREFOR

(75) Inventor: Chunming Zhang, Midland, MI (US)

(73) Assignee: Sumitomo Chemical Company, Limited, Tokyo (JP)

( * ) Notice: Subject to any disclaimer, the term of this patent is extended or adjusted under 35 U.S.C. 154(b) by 547 days.

(21) Appl. No.: 10/844,250

(22) Filed: May 12, 2004

(65) Prior Publication Data

US 2004/0229925 A1  Nov. 18, 2004

Related U.S. Application Data

(60) Provisional application No. 60/471,040, filed on May 16, 2003.

(51) Int. Cl.
C07D 417/14 (2006.01)
(52) U.S. Cl. .................................................. 548/126
(58) Field of Classification Search ................ 548/162
See application file for complete search history.

(56) References Cited

U.S. PATENT DOCUMENTS

| | | | | |
|---|---|---|---|---|
| 5,708,130 A | 1/1998 | Woo et al. | ................... | 528/397 |
| 5,777,070 A | 7/1998 | Inbasekaran et al. | ....... | 528/488 |
| 6,353,083 B1 | 3/2002 | Inbasekaran et al. | ....... | 528/295 |

FOREIGN PATENT DOCUMENTS

| | | |
|---|---|---|
| WO | WO 01/49768 | 7/2001 |
| WO | WO 02/059121 | 8/2002 |
| WO | WO 03/020790 | 3/2003 |
| WO | WO 2004/002970 | 1/2004 |
| WO | WO 2004/003108 | 1/2004 |

OTHER PUBLICATIONS

E. Negishi et al., *J. Org. Chem.* 42, 1821, 1977.
M. Karikomi et al., *J. Am. Chem. Soc.*, vol. 117, 1995, pp. 6791-6792.
Kumada et al., *J. of Amer. Chemical Society*, vol. 94, 1972, p. 4374-4376.
Miyaura et al., *Chem. Reviews*, vol. 95, 1995, p. 2457-2483.
M. Jayakannan, et al., *Journal of Polymer Science: Part A: Polymer Chemistry*, vol. 40, 2360-2372, 2002.
M. Jayakannan, et al., *Journal of Polymer Science: Part A: Polymer Chemistry*, vol. 40, 251-261, 2002.
van Mullekom, et al., *Chem. Europ. J.*, vol. 4, No. 7, 1998, pp. 1235-1243.
van Mullekom, et al., *Polymer Preprints*, vol. 39, No. 2, 1998, pp. 1002-1003.
Redecker, et al., *Applied Physics Letters*, vol. 73, 1998, p. 1565-1567.
Kitamura et al., Chem. Materl, vol. 8, 1996, p. 570-578.
Svensson et al., "Synthesis and properties of alternating polyfluorene copolymers with redshifted absorption for use in solar cells", *Synthetic Metals*, vol. 135-136, 2003, pp. 137-138.
Yamashita et al., "Novel electron acceptors containing thiadiazole and thiophene units", *Synthetic Metals*, vol. 133-134, 2003, pp. 341-343.
Van Mullekom et al., "Band-gap Engineering of Donor—Acceptor-subsitutted π-Conjugated Polymers", *Chem. Eur. J.*, vol. 4, No. 7, 1998, pp. 1235-1243.
Van Mullekom et al., "Band-gap Engineering of Donor-Acceptor Conjugated Polymers", *Polymer Preprints*, vol. 39, No. 2, 1998, pp. 1002-1003.
Karikomi et al., "New Narrow-bandgap Polymer Composed on Benzobis(1,2,5-thiadiazole) and Thiophenes," *J. Am. Chem. Soc.*, 1995, vol. 117, pp. 6791-6792.
Negishi, Abstract of Talk at Purdue University, 1998.

*Primary Examiner*—Kamal A. Saeed
(74) *Attorney, Agent, or Firm*—Sughrue Mion, PLLC

(57) ABSTRACT

The present invention is directed to a method for preparing a 4,7-bis(5-halothien-2-yl)-2,1,3-benzothiadiazole, more particularly, 4,7-bis(5-bromothien-2-yl)-2,1,3-benzothiadiazole, and a precursor therefor, namely, a 4,7-bis(thien-2-yl)-2,1,3-benzothiadiazole. The precursor is prepared by contacting in the presence of a palladium catalyst and a solvent a 4,7-dihalo-2,1,3-benzothiadiazole with a thienyl group adding reagent, which can either be a 2-thienylzinc halide, a 2-thienylmagnesium halide, or a 2-thiopheneboronic acid, under such conditions as to form 4,7-bis(thien-2-yl)-2,1,3-benzothiadiazole. The precursor can then be halogenated, preferably brominated, to form the desired dibrominated product, which is a particularly suitable monomer for the preparation of a copolymer of a 9,9-disubstituted fluorene. This copolymer is useful, for example, in polymeric light emitting diode (pLED) applications.

14 Claims, No Drawings

PROCESS FOR PREPARING A 4,7-BIS(5-HALOTHIEN-2-YL)-2,1,3-BENZO-THIADIAZOLE AND A PRECURSOR THEREFOR

CROSS-REFERENCE STATEMENT

This application claims the benefit of U.S. Provisional application No. 60/471,040 filed May 16, 2003.

This invention relates to a process for preparing a 4,7-bis(5-halothien-2-yl)-2,1,3 benzothiadiazole, more particularly 4,7-bis(5-halothien-2-yl)-2,1,3 benzothiadiazole, and a precursor therefor.

BACKGROUND

Poly(9,9-disubstituted-fluorene-2,7-diyls) (polyfluorenes) exhibit the optical and electronic properties of inorganic semiconductors because of the presence of delocalized electrons in the π-orbital system. These polymers are especially desirable because the backbone is resistant to chemical and photochemical degradation and the fluorene structural units are locked into a planar-like configuration. Moreover, substituents at the C9 position of fluorene may be chosen to modify physical, chemical, and electronic properties without introducing torsional strain between adjacent fluorene structural units that would otherwise be disruptive to delocalization of the π-orbital system. For example, poly(9,9-di-n-octylfluorene-2,7-diyl), described in U.S. Pat. No. 5,708,130 by Woo et al. has been shown to by Grice, et al. (Applied Physics Letters, Vol. 73, 1998, p. 629–631) be an effective emitter for a blue light emitting diode (LED) and by Redecker, et al. (Applied Physics Letters, Vol. 73, 1998, p. 1565–1567) to exhibit advantageously high carrier mobility.

Methods to further modify optical and electronic properties of polyfluorenes through copolymerization of 9,9-disubstituted-fluorenes and various comonomers containing delocalized π-system electrons are described in U.S. Pat. Nos. 5,777,070, 5,708,130, and 6,353,083. An example of a particularly desirable comonomer is 4,7-bis(5-bromothien-2-yl)-2,1,3-benzothiadiazole, described in WO 00/46321, and having the following chemical structure:

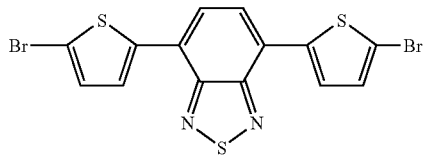

The 4,7-bis(5-bromothien-2-yl)-2,1,3-benzothiadiazole is traditionally prepared from 4,7-bis(thien-2-yl)-2,1,3-benzothiadiazole, which in turn is prepared by the Stille coupling reaction of 4,7-dibromo-2,1,3-benzothiadiazole with tributyl(thien-2-yl)stannane as described by Kitamura et al., Chem. Mater., Vol. 8, 1996, pp. 570–578. Unfortunately, tributyl(thien-2-yl) stannane is a highly toxic and costly material that produces a toxic by-product tributyltin bromide. The process is further disadvantaged because the subsequent bromination reaction is carried out in a mixture of N-bromosuccinimide, chloroform, and acetic acid, which requires numerous crystallizations of the product to obtain a suitably pure material in the subsequent copolymerization reaction.

Accordingly, it would be advantageous to have a method of preparing 4,7-bis(5-bromothien-2-yl)-2,1,3-benzothiadiazole more safely and efficiently than methods described in the art.

SUMMARY OF INVENTION

The present invention addresses a need in the art by providing in one aspect a method for preparing a 4,7-bis(thien-2-yl)-2,1,3-benzothiadiazole comprising the step of reacting, in the presence of a palladium catalyst and a first solvent a) a 4,7-dihalo-2,1,3-benzothiadiazole with b) a thienyl group adding reagent selected from the group consisting of a 2-thienylzinc halide, a 2-thienylmagnesium halide, a 2-thienyllithium, and a 2-thiopheneboronic acid; under such conditions as to form a 4,7-bis(thien-2-yl)-2,1,3-benzothiadiazole, with the proviso that when the thienyl group adding reagent is 2-thiopheneboronic acid, the reaction is carried out in the presence of a base.

In a second aspect, the present invention is a method for preparing 4,7-bis(5-bromothien-2-yl)-2,1,3-benzothiadiazole comprising the step of reacting 4,7-bis(thien-2-yl)-2,1,3-benzothiadiazole with a brominating agent in the presence of o-dichlorobenzene under such conditions as to form 4,7-bis(5-bromothien-2-yl)-2,1,3-benzothiadiazole.

DETAILED DESCRIPTION

In the first aspect of the present invention, a 4,7-dihalo-2,1,3-benzothiadiazole, preferably 4,7-dibromo-2,1,3-benzothiadiazole, and a thienyl group adding reagent, which is either a 2-thienylzinc halide, a 2-thienylmagnesium halide, or a 2-thiopheneboronic acid, are reacted together in the presence of a palladium catalyst under such conditions to form a 4,7-bis(thien-2-yl)-2,1,3-benzothiadiazole. As used herein, the terms "a 2-thienylzinc halide," "a 2-thienylmagnesium halide," and "a 2-thiopheneboronic acid" refer to substituted and unsubstituted thienyl group adding reagents. When no article precedes the terms, "2-thienylzinc halide" and "2-thienylmagnesium halide" refers to unsubstituted 2-thienylzinc halides and 2-thienylmagnesium halides respectively, i.e., there is no substitution at either the 3- or 4-positions of the thiophene ring, while "2-thiopheneboronic acid" refers to the compound 2-thiopheneboronic acid.

Similarly, the term "a 4,7-dihalo-2,1,3-benzothiadiazole" is used herein to refer to substituted and unsubstituted 4,7-dihalo-2,1,3-benzothiadiazoles. Where no article precedes this term, "4,7-dihalo-2,1,3-benzothiadiazole" refers to unsubstituted 4,7-dihalo-2,1,3-benzothiadiazoles, i.e., there is no substitution at either the 5- or 6-positions.

As used herein, the term "thienyl group adding reagent" describes a reagent that replaces the halo groups in the 4,7-dihalo-2,1,3-benzothiadiazole with thienyl groups or substituted thienyl groups. The thienyl group adding reagent may include substituents on the thiophene ring such as alkyl groups, particularly methyl groups, at the 3- or 4-position or both the 3- and 4-position.

Where the thienyl group adding reagent is a 2-thienylzinc halide, the reaction is carried out by a modified Negishi cross coupling reaction. See E. Negishi et al., *J. Org. Chem.* 42, 1821 (1977). In the present case, a 4,7-dihalo-2,1,3-benzothiadiazole, and a 2-thienylzinc halide are cross coupled in the presence of a palladium catalyst and one or more solvents.

The 2-thienylzinc halide may be unsubstituted or a 3- or 4-substituted-2-thienylzinc halide or a 3,4-disubstituted-2-thienylzinc halide. Where the 2-thienylzinc halide is substituted or disubstituted, the substitutent is preferably alkyl, more preferably methyl. In a preferred method of preparing the 2-thienylzinc halide, n-butyllithuim in tetrahydrofuran is first added slowly to a solution of a thiophene in tetrahydrofuran. After sufficient reaction time, preferably for from about 1 to about 10 hours, and preferably at room temperature, the mixture is advantageously cooled to about 0° C., whereupon an anhydrous zinc halide is added. The mixture is then brought back to about room temperature and stirring is continued until substantial completion of the reaction, preferably from about 30 minutes to about 2 hours.

It is also possible and sometimes preferable to prepare or generate in situ the 2-thienylzinc halide by way of a lithium or a Grignard intermediate. For example, a 2-bromo-3-alkylthiophene can be reacted with magnesium to make the Grignard reagent, which can be converted to the corresponding 3-alkyl-2-thienylzinc halide by treating the Grignard reagent with a zinc halide, preferably zinc chloride.

A preferred method of preparing a 3-methyl-2-thienylzinc halide is reacting 2-bromo-3-methylthiophene with magnesium to generate the Grignard reagent, which is then conveniently reacted with a zinc halide, preferably zinc chloride to generate the desired product. A preferred method of preparing a 4-methyl-2-thienylzinc halide is reacting 3-methylthiophene with n-butyllithium in the presence of an amine such as N, N, N', N'-tetramethylethylenediamine (TEMDA) or diisopropylamine to form a 4-methyl-2-thienyllithium intermediate, then reacting this intermediate with a zinc halide, preferably zinc chloride to generate the desired product The halide of the thienylzinc halide may be an iodide, a bromide, or a chloride and is preferably a chloride. The palladium catalyst used in the coupling reaction can be a Pd(0) complex or Pd II salt with a phosphine ligand. Examples of suitable palladium catalysts include, but are not limited to, $Pd(Ph_3P)_4$; $Pd_2(dba)_3$ or $Pd(OAc)_2$ plus $Ph_3P$. Preferably the catalyst is a combination of $Pd(OAc)_2$ and $Ph_3P$. The mole-to-mole ratio of $Pd(OAc)_2$ and $Ph_3P$ preferably ranges from about 1:1 to 1:4.

The modified Negishi coupling reaction can be run in a variety of solvents including tetrahydrofuran, dimethoxyethane, toluene, or xylene or combinations thereof, with tetrahydrofuran being a more preferred solvent. This reaction is preferably carried out at a temperature of not lower than 5° C., more preferably not lower than 10° C., and most preferably not lower than 15° C.; and preferably not higher than 100° C., more preferably not higher than 60° C., and most preferably not higher than 25° C.

Where the thienyl group adding reagent is a 2-thienylmagnesium halide or a 2-thienyllithium, the 4,7-bis(thien-2-yl)-2,1,3-benzothiadiazole is prepared using a modification of the Kumada cross-coupling reaction, described by Kumada et al. in Journal of the American chemical Society, Vol. 94, pp. 4374–4376(1972). In this modification, a 4,7-dihalo-2,1,3-benzothiadiazole, preferably, 4,7-dibromo-2,1,3-benzothiadiazole, is contacted with a 2-thienylmagnesium halide (commercially available from Aldrich) or 2-thienyllithium in the presence of a palladium catalyst and, preferably, a zinc halide, preferably zinc chloride, in one or more solvents.

Where the thienyl group adding reagent is a 2-thiopheneboronic acid, the 4,7-bis(thien-2-yl)-2,1,3-benzothiadiazole is prepared using a modification of the Suzuki cross-coupling reaction, described by Miyava et al. in Chemical Revews, Vol. 95, pp. 2457–2483 (1995). In this modification, a 4,7-dihalo-2,1,3-benzothiadiazole, preferably, 4,7-dibromo-2,1,3-benzothiadiazole, is contacted with a 2-thiopheneboronic acid (commercially available from Aldrich) in the presence of a palladium catalyst and a base in one or more solvents. The 2-thiopheneboronic acid may be unsubstituted or a 3- or 4-substituted-2-thiopheneboronic acid or a 3,4-disubstituted-2-thiopheneboronic acid, with unsubstituted 2-thiopheneboronic acid being preferred. Preferred substituents are alkyl groups, more preferably methyl groups.

For either coupling reaction, the 4,7-dihalo-2,1,3-benzothiadiazole may be unsubstituted or a 5- or 6-substituted-4,7-dihalo-2,1,3-benzothiadiazole or a 5,6-disubstituted-4,7-dihalo-2,1,3-benzothiadiazole, with unsubstituted being preferred. Preferred substituents are alkyl groups, more preferably methyl group.

The palladium catalyst used for this reaction is the same as described for the Negishi coupling reaction.

Examples of preferred bases are inorganic bases (solid or aqueous) including, but not restricted to, hydroxides and carbonates, with carbonates such as $K_2CO_3$, $Na_2CO_3$ being preferred.

Preferred solvents used to make the 4,7-bis(thien-2-yl)-2,1,3-benzothiadiazole include, but are not restricted to, tetrahydrofuran, 1,2-dimethoxyethane, toluene, and xylene, and combinations thereof, with tetrahydrofuran and toluene being more preferred solvents.

The reaction can be carried out at any suitable temperature, preferably from about −5° C. to about 100° C.

The monomer, a 4,7-bis(5-halothien-2-yl)-2,1,3-benzothiadiazole, can be prepared by halogenation, preferably bromination of 4,7-bis(thien-2-yl)-2,1,3-benzothiadiazole with a halogenating agent, preferably a brominating agent under conditions sufficient to produce the desired product. Examples of suitable halogenating agents include, but are not restricted to bromine, N-bromosuccinimide (NBS), 1,3-dibromo-5,5-dimethylhydantoin, chlorine, and iodine, with NBS being preferred. Suitable solvents for this reaction include, but are not restricted to dimethylformamide (DMF), $CHCl_3$, 1,2-dichloroethane, chlorobenzene, and o-dichlorobenzene, and combinations thereof. Preferred solvents include $CHCl_3$, chlorobenzene, and o-dichlorobenzene, with o-dichlorobenzene being more preferred. The reaction is carried out under conditions sufficient to form the desired product, preferably at a temperature in the range of not lower than −10° C., more preferably not lower than 40° C., and most preferably not lower than 50° C.; and preferably not higher than 100° C., more preferably not higher than 80° C., and most preferably not higher than 60° C. Suitable solvents for purification of 4,7-bis(5-bromothien-2-yl)-2,1,3-benzothiadiazole by recrystallization include, but are not restricted to, DMF, chlorobenzene and o-dichlorobenzene, and combinations thereof, with o-dichlorobenzene being more preferred. Temperatures for recrystallization range from about 20 to about 150° C.

In a second aspect of the present invention, 4,7-bis(5-bromothien-2-yl)-2,1,3-benzothiadiazole is prepared using o-dichlorobenzene and preferably without any other solvents. It has been surprisingly discovered that when o-dichlorobenzene is used, a highly pure product, preferably at least 98% pure, more preferably at least 99% pure, most preferably at least 99.5% pure, can be prepared at yields of preferably at least 70%, more preferably at least 80%, and most preferably at least 85%.

The following examples are included for illustrative purposes only and do not limit the scope of the claims. Unless otherwise stated, all parts and percentages are by weight.

EXAMPLE 1

Preparation of 4,7-Bis(thien-2-yl)-2,1,3-benzothiadiazole by Negishi Cross-Coupling Reaction The thien-2-yl-zinc chloride was prepared by adding n-butyllithium (2.5 M in hexane, 30 mL, 75.0 mmol) dropwise to a stirred solution of thiophene (6.5 g, 77.0 mmol) in THF (50 mL) at 0° C. under nitrogen over 15 minutes. Upon completion of addition, the solution was allowed to warm to room temperature with stirring. After stirring for 3 hours at room temperature, the mixture was cooled to 0° C. again and anhydrous zinc chloride (10.05 g, 75 mmol) was added in one portion. The resultant mixture was allowed to warm to room temperature and was stirred for an additional 1 hour.

This resulting thien-2-yl-zinc chloride solution was added via a cannula to a stirred mixture of 4,7-dibromo-2,1,3-benzothiadiazole (10.28 g, 35 mmol), Pd(OAc)$_2$ (39.2 mg, 0.175 mmol) and Ph$_3$P (91.7 mg, 0.35 mmol) in THF (50 mL) at room temperature under nitrogen over 1 hour 15 minutes. The mixture was stirred for an additional 20 minutes at room temperature and quenched with aqueous HCl (3 N, 80 mL). After stirring for 30 minutes, the crude product was collected by filtration, rinsed with water (100 mL) and ethanol (50 mL) and dried. Crude product 9.47 g (98% purity by GC area) was obtained, which was recrystallized from toluene/ethanol (40 mL/120 mL) to pure product (9.04 g, 86% yield).

EXAMPLE 2

Preparation of 4,7-Bis(thien-2-yl)-2,1,3-benzothiadiazole by a Suzuki Cross-Coupling Reaction To a 1-liter reactor equipped with condenser, agitator, thermometer, and N$_2$ inlet and outlet, was added Pd(OAc)$_2$ (224 mg, 1.0 mmol), Ph$_3$P (524 mg, 2.0 mmol), and THF (100 mL) under nitrogen. The mixture was stirred at room temperature until all solids were dissolved (10 minutes) at which time 4,7-dibromo-2,1,3-benzothiadiazole (58.8 g, 0.2 mmol), 2-thiopheneboronic acid (64.0 g, 0.50 mol), THF (300 mL), and Na$_2$CO$_3$ (2 M, 250 mL) were added to the reactor. The mixture was heated to reflux with stirring for 5 hours, after which the mixture was allowed to cool to room temperature, then poured into water (400 mL) to precipitate the product. The crude product was collected by filtration and rinsed with water (500 mL) and ethanol (100 mL). After air drying, the crude product was recrystallized with toluene/ethanol to yield 54.5 g of 99.5% pure product. M.p. 121–122° C. $^1$H NMR spectroscopic analysis: (300 MHz/DMSO-d$_6$) 8.25 (m, 2H), 8.10 (s,2 H), 7.77 (d, J=5.0, 2H), 7.28 (m,J=5.02 H).

EXAMPLE 3

Preparation of 4,7-Bis(5-bromothien-2-yl)-2,1,3-benzothiadiazole

A 5-liter reactor equipped with agitator, condenser and thermometer, were charged with o-dichlorobenzene (3 L), 4,7-bis(thien-2-yl)-2,1,3-benzothiadiazole (150.0 g, 0.5 mol) and NBS (170.0 g, 0.95 mol). The mixture was heated slowly to 55° C. After stirring at 55° C. for 3 hours, the resulting slurry was heated to 150° C. to dissolve the solids. When all solids disappeared, the mixture was allowed to cool to room temperature. Stirring was stopped and the supernatant liquid was drawn off by vacuum (aspirator) using a glass fritted sparge tube (removing as much liquid as possible). The remaining wet cake was slurried/stirred with water (2×2, 500 mL) and ethanol (500 mL), and each time the supernatant liquid was drawn off by vacuum as described above. The wet cake was dried by passing a nitrogen stream over the solids, followed by pulling vacuum on the vessel. The crude product which had 98.4% purity by GC area, was recrystallized from o-dichlorobenzene as follows: 1,200 mL of o-dichlorobenzene was added to the reactor. The mixture was heated with stirring to 150° C. until all solids were dissolved, then allowed to cool to room temperature. The liquid was drawn off in vacuo using a glass fritted sparge tube, the reactor was recharged with 1,200 mL of o-dichlorobenzene and the above recrystallization process repeated. The wet cake was washed with o-dichlorobenzene (100 mL) and ethanol (400 mL) and dried at 50° C./2–3 mmHg overnight. Pure product (194.2 g) was obtained in 84.8% yield, which was of 99.7% of purity as measured by GC area. M.p.247–248° C., $^1$H NMR spectroscopic analysis: (300 MHz/DMSO-d$_6$) 8.16 (s, 2H), 7.97(m, 2H), 7.39 (m, 2H).

What is claimed is:

1. A method of preparing a 4,7-bis(thien-2-yl)-2,1,3-benzothiadiazole comprising the step of reacting, in the presence of a palladium catalyst and a first solvent a) a 4,7-dihalo-2,1,3-benzothiadiazole with b) a thienyl group adding reagent selected from the group consisting of a 2-thienylzinc halide, a thienylmagnesium halide, a 2-thienyllithium and a 2-thiopheneboronic acid; under such conditions as to form a 4,7-bis(thien-2-yl)-2,1,3-benzothiadiazole, with the proviso that when the thienyl group adding reagent is a 2-thiopheneboronic acid, the reaction is carried out in the presence of a base.

2. The method of claim 1 wherein the 4,7-dihalo-2,1,3-benzothiadiazole is 4,7-dibromo-2,1,3-benzothiadiazole.

3. The method of claim 2 wherein the thienyl group adding reagent is a 2-thienylzinc halide and the palladium catalyst includes a Pd(0) complex or a Pd(II) salt and a phosphine ligand, wherein the 2-thienylzinc halide is selected from the group consisting of a 3-alkyl-2-thienylzinc halide, a 4-alkyl-2-thienylzinc halide, and a 3,4-dialkyl-2-thienylzinc halide, and 2-thienylzinc halide.

4. The method of claim 3 wherein the 2-thienylzinc halide is 2-thienylzinc chloride or a 4-methyl-2-thienylzinc halide or a 3-methyl-2-thienylzinc halide.

5. The method of claim 1 wherein the first solvent is selected from the group consisting of tetrahydrofuran, 1,2-dimethoxyethane, toluene, and xylene.

6. The method of claim 1 wherein the thienyl group adding reagent is a 2-thiopheneboronic acid and the palladium catalyst includes a Pd(0) complex or a Pd(II) salt and a phosphine ligand.

7. The method of claim 6 wherein the 2-thiopheneboronic acid is selected from the group consisting of 2-thiopheneboronic acid, a 3-alkyl-2-thiopheneboronic acid, a 4-alkyl-2-thiopheneboronic acid, and a 3,4-dialkyl-2-thiopheneboronic acid.

8. The method of claim 7 wherein the 2-thiopheneboronic acid is 2-thiopheneboronic acid and wherein the base includes a carbonate or hydroxide.

9. The method of claim 1 which further includes the step of reacting the 4,7-bis(thien-2-yl)-2,1,3-benzothiadiazole with a halogenating agent in a second solvent under such conditions to form 4,7-bis(5-halothien-2-yl)-2,1,3-benzothiadiazole.

10. The method of claim 9 wherein the halogenating agent is a brominating agent selected from the group consisting of bromine, N-bromosuccinimide, and 1,3-dibromo-5,5-dimethylhydanation.

11. The method of claim 10 wherein halogenating agent is bromine and the second solvent is selected from the group consisting of $CHCl_3$, chlorobenzene, and o-dichlorobenzene, and wherein the reaction is carried out at a temperature not lower than less than 5° C. and not higher than 100° C.

12. The method of claim 11 wherein the second solvent is o-dichlorobenzene.

13. A method for preparing 4,7-bis(5-bromothien-2-yl)-2,1,3-benzothiadiazole comprising the step of reacting 4,7-bis(thien-2-yl)-2,1,3-benzothiadiazole with a brominating agent in the presence of o-dichlorobenzene under such conditions as to form 4,7-bis(5-bromothien-2-yl)-2,1,3-benzothiadiazole at a purity of at least 95%.

14. The method of claim 13 wherein the brominating agent is NBS and the purity is at least 98%.

* * * * *